US012211610B2

(12) United States Patent
Yousfi et al.

(10) Patent No.: US 12,211,610 B2
(45) Date of Patent: *Jan. 28, 2025

(54) SYSTEMS AND METHODS OF AUTOMATICALLY PROCESSING ELECTRONIC IMAGES ACROSS REGIONS

(71) Applicant: PAIGE.AI, Inc., New York, NY (US)

(72) Inventors: Razik Yousfi, Brooklyn, NY (US); Peter Schueffler, Munich (DE); Thomas Fresneau, Oro Valley, AZ (US); Alexander Tsema, New York, NY (US)

(73) Assignee: Paige.AI, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/461,617

(22) Filed: Sep. 6, 2023

(65) Prior Publication Data

US 2023/0410987 A1   Dec. 21, 2023

Related U.S. Application Data

(63) Continuation of application No. 17/805,992, filed on Jun. 8, 2022, now Pat. No. 11,791,036, which is a
(Continued)

(51) Int. Cl.
*G16H 30/40* (2018.01)
*G06F 18/2413* (2023.01)
(Continued)

(52) U.S. Cl.
CPC ......... *G16H 30/40* (2018.01); *G06F 18/2413* (2023.01); *G06N 20/00* (2019.01);
(Continued)

(58) Field of Classification Search
CPC ........ G16H 10/60; G16H 30/20; G16H 30/40; G16H 50/20; G06F 18/2413; G06N 20/00; G06T 7/0012

See application file for complete search history.

(56) References Cited

U.S. PATENT DOCUMENTS 11,010,610 B2   5/2021  Stumpe
2010/0111396 A1  5/2010  Boucheron
(Continued)

FOREIGN PATENT DOCUMENTS

WO   2020222985 A1   11/2020

OTHER PUBLICATIONS

Bentaieb et al., "Deep Learning Models for Digital Pathology", ArXiv abs/1910.12329 (2019): pp. 1-58 (Year: 2019).
(Continued)

*Primary Examiner* — Ping Y Hsieh
*Assistant Examiner* — Jose M Torres
(74) *Attorney, Agent, or Firm* — Bookoff McAndrews, PLLC

(57) ABSTRACT

Systems and methods are disclosed for using an integrated computing platform to view and transfer digital pathology slides using artificial intelligence, the method including receiving at least one whole slide image in a cloud computing environment located in a first geographic region, the whole slide image depicting a medical sample associated with a patient, the patient being located in the first geographic region; storing the received whole slide image in a first encrypted bucket; applying artificial intelligence to perform a classification of the at least one whole slide image, the classification comprising steps to determine whether portions of the medical sample depicted in the whole slide image are healthy or diseased; based on the classification of the at least one whole slide image, generating metadata associated with the whole slide image; and storing the metadata in a second encrypted bucket.

20 Claims, 11 Drawing Sheets

Related U.S. Application Data continuation of application No. 17/530,372, filed on Nov. 18, 2021, now Pat. No. 11,386,989, which is a continuation of application No. 17/200,563, filed on Mar. 12, 2021, now Pat. No. 11,211,160.

(60) Provisional application No. 62/989,095, filed on Mar. 13, 2020.

(51) Int. Cl.
*G06N 20/00* (2019.01)
*G06T 7/00* (2017.01)
*G16H 10/60* (2018.01)
*G16H 30/20* (2018.01)

(52) U.S. Cl.
CPC ........... *G06T 7/0012* (2013.01); *G16H 10/60* (2018.01); *G16H 30/20* (2018.01)

(56) References Cited

U.S. PATENT DOCUMENTS

| | | | |
|---|---|---|---|
| 2013/0208966 A1 | 8/2013 | Zhao et al. |
| 2013/0315465 A1 | 11/2013 | Cosatto et al. |
| 2014/0334696 A1 | 11/2014 | Gholap |
| 2016/0147945 A1 | 5/2016 | MacCarthy et al. |
| 2017/0293717 A1 | 10/2017 | Yu |
| 2018/0232883 A1 | 8/2018 | Sethi et al. |
| 2019/0073510 A1 | 3/2019 | West et al. |
| 2019/0114770 A1 | 4/2019 | Song et al. |
| 2019/0156159 A1 | 5/2019 | Kopparapu |
| 2019/0198160 A1 | 6/2019 | Barral |
| 2019/0286880 A1 | 9/2019 | Jackson et al. |
| 2019/0295252 A1 | 9/2019 | Fuchs et al. |
| 2019/0347557 A1 | 11/2019 | Khan |
| 2020/0097727 A1 | 3/2020 | Stumpe |
| 2020/0160032 A1 | 5/2020 | Allen et al. |
| 2020/0211189 A1 | 7/2020 | Yip et al. |
| 2020/0258223 A1 | 8/2020 | Yip et al. |
| 2020/0272864 A1 | 8/2020 | Faust et al. |
| 2020/0388029 A1 | 12/2020 | Saltz et al. |
| 2021/0018742 A1 | 1/2021 | Stumpe |
| 2021/0074425 A1 | 3/2021 | Carter et al. |
| 2021/0074429 A1 | 3/2021 | Singhal et al. |

OTHER PUBLICATIONS

International Search Report and Written Opinion dated Jun. 11, 2020 in counterpart International Patent Application No. PCT/US2021/022211 (13 pages, in English).

Parwani, "Next generation diagnostic pathology: use of digital pathology and artificial intelligence tools to augment a pathological diagnosis", Diagnostic Pathology (2019) 14:138, pp. 1-3 (Year: 2019).

Puttapirat et al., "OpenHI2—Open source histopathological image platform", arXiv:2001.05158, 2020, pp. 1-6 (Year: 2020).

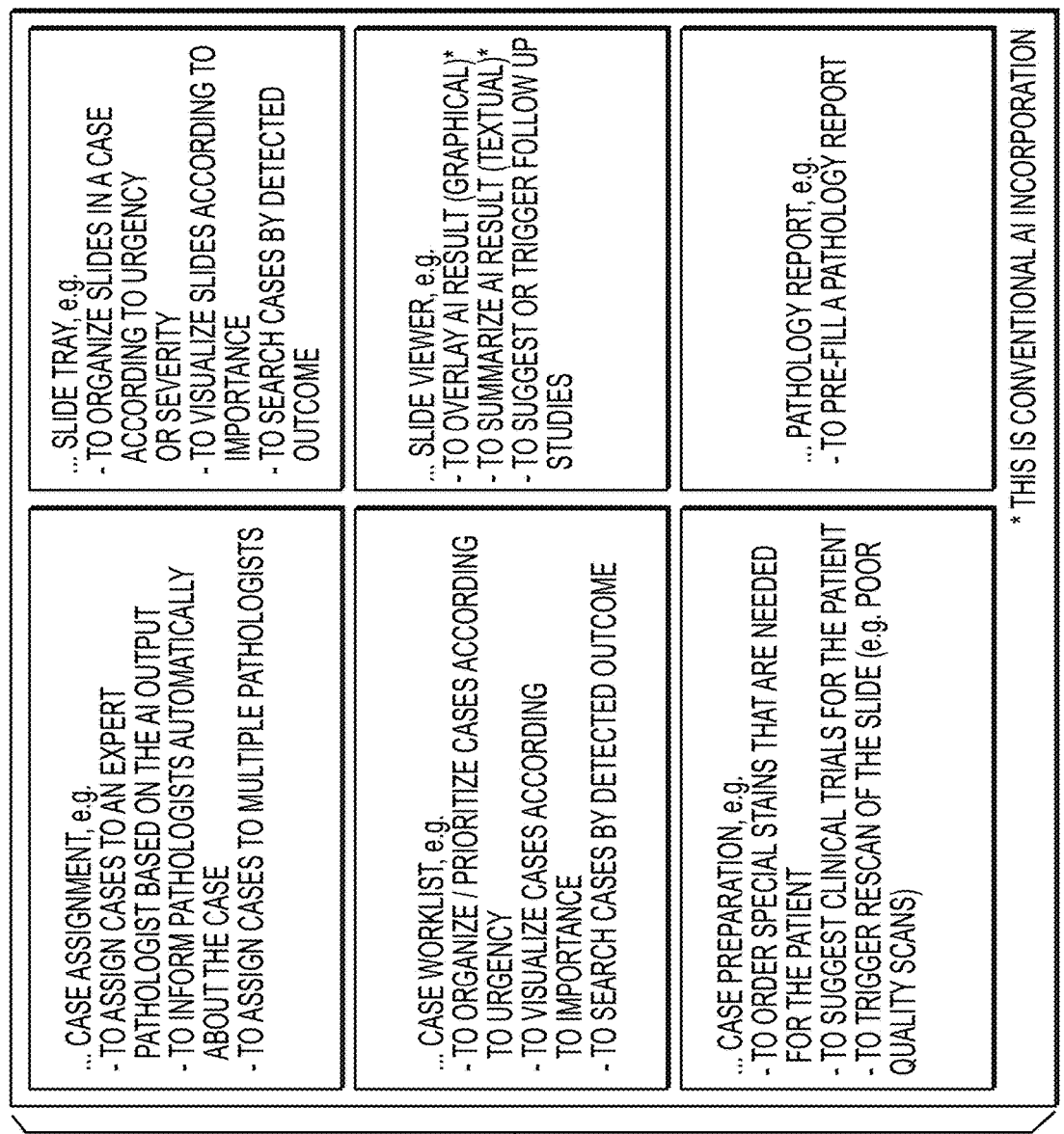
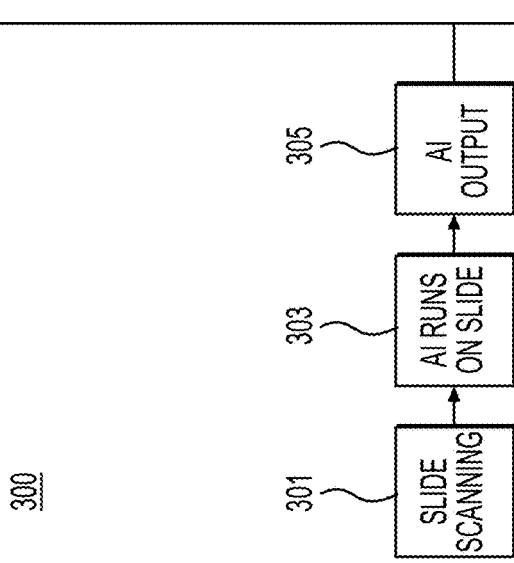
FIG. 3

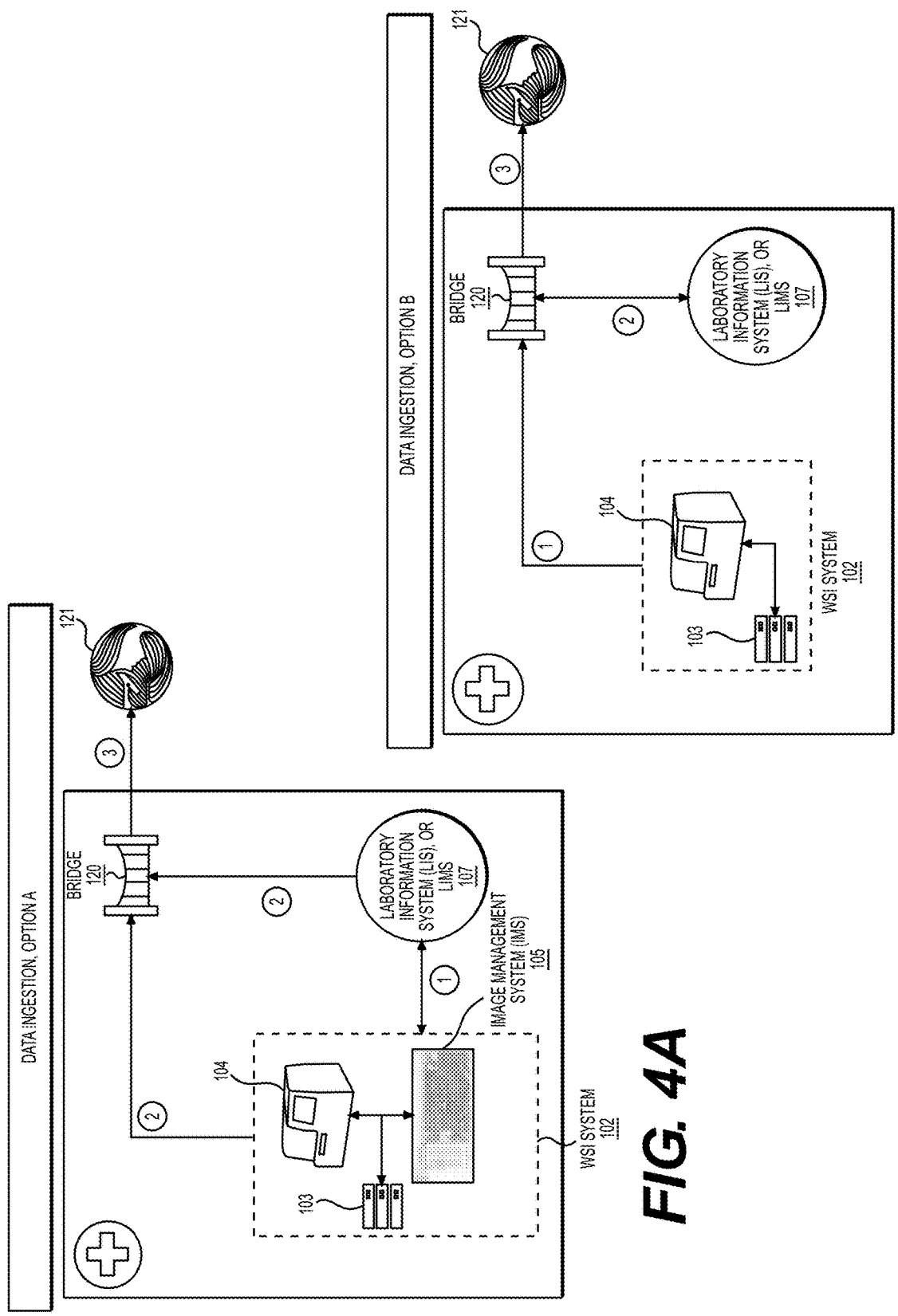

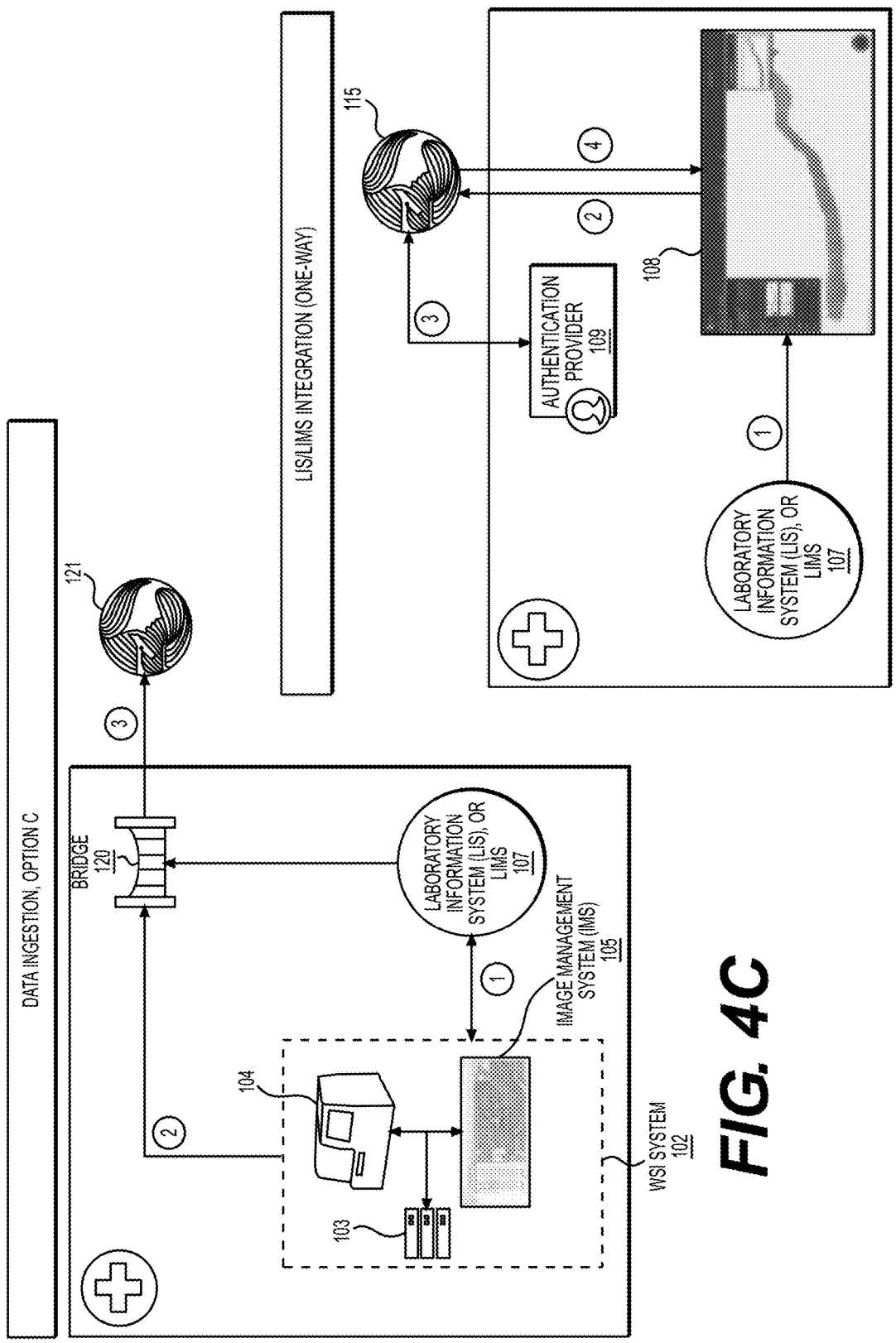

SYSTEMS AND METHODS OF AUTOMATICALLY PROCESSING ELECTRONIC IMAGES ACROSS REGIONS

CROSS-REFERENCE TO RELATED APPLICATION(S)

This application claims priority to U.S. application Ser. No. 17/805,992, filed on Jun. 8, 2022, which is a continuation of U.S. application Ser. No. 17/530,372, now U.S. Pat. No. 11,386,989, filed on Nov. 18, 2021, which is a continuation of U.S. application Ser. No. 17/200,563, now U.S. Pat. No. 11,211,160, filed on Mar. 12, 2021, which claims priority to U.S. Provisional Application No. 62/989,095 filed Mar. 13, 2020, the entire disclosures of which are hereby incorporated herein by reference in their entireties.

FIELD OF THE DISCLOSURE

Various embodiments of the present disclosure pertain generally to computational pathology devices for processing electronic images. More specifically, particular embodiments of the present disclosure relate to computational pathology devices configured to build clinical-grade products for the treatment of cancer. The present disclosure further provides systems and methods for diagnostic accuracy, reliability, efficiency and accessibility.

BACKGROUND

The present disclosure describes computational pathology processes and devices configured to be used to build clinical-grade products that may transform the diagnosis and treatment of cancer. By using computational pathology, pathologists may improve their diagnostic accuracy, reliability, efficiency, and accessibility. For example, a device may detect slides as being suspicious for cancer, allowing pathologists to check their initial assessments before rendering a final diagnosis. Computational pathology processes and devices of the present disclosure may provide an integrated platform allowing the ingestion, processing, and viewing of digital pathology images via a web-browser, while integrating with a Laboratory Information System (LIS).

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for using an integrated computing platform to view and transfer digital pathology slides using artificial intelligence (AI).

A method for using an integrated computing platform to view and transfer digital pathology slides using artificial intelligence (AI) includes: receiving at least one whole slide image in a cloud computing environment located in a first geographic region, the whole slide image depicting a medical sample associated with a patient, the patient being located in the first geographic region; storing the received whole slide image in a first encrypted bucket; applying artificial intelligence to perform a classification of the at least one whole slide image, the classification comprising steps to determine whether portions of the medical sample depicted in the whole slide image are healthy or diseased; based on the classification of the at least one whole slide image, generating metadata associated with the whole slide image; and storing the metadata in a second encrypted bucket.

A system for using an integrated computing platform to view and transfer digital pathology slides using artificial intelligence (AI) includes: a memory storing instructions; and at least one processor executing the instructions to perform a process including receiving at least one whole slide image in a cloud computing environment located in a first geographic region, the whole slide image depicting a medical sample associated with a patient, the patient being located in the first geographic region; storing the received whole slide image in a first encrypted bucket; applying artificial intelligence to perform a classification of the at least one whole slide image, the classification comprising steps to determine whether portions of the medical sample depicted in the whole slide image are healthy or diseased; based on the classification of the at least one whole slide image, generating metadata associated with the whole slide image; and storing the metadata in a second encrypted bucket.

A non-transitory computer-readable medium storing instructions that, when executed by a processor, cause the processor to perform a method for using an integrated computing platform to view and transfer digital pathology slides using artificial intelligence (AI), the method including: receiving at least one whole slide image in a cloud computing environment located in a first geographic region, the whole slide image depicting a medical sample associated with a patient, the patient being located in the first geographic region; storing the received whole slide image in a first encrypted bucket; applying artificial intelligence to perform a classification of the at least one whole slide image, the classification comprising steps to determine whether portions of the medical sample depicted in the whole slide image are healthy or diseased; based on the classification of the at least one whole slide image, generating metadata associated with the whole slide image; and storing the metadata in a second encrypted bucket.

It is to be understood that both the foregoing general description and the following detailed description are exemplary and explanatory only, and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3 is a workflow illustrating an exemplary method for use of the platform with an artificial intelligence (AI) output, according to an exemplary embodiment of the present disclosure.

FIGS. 4A-C are exemplary architectures of a data ingestion appliance and integrations of the data ingestion appliance, according to exemplary embodiments of the present disclosure.

FIGS. 5A-C are exemplary architecture of a LIS and integration of the LIS, according to exemplary embodiments of the present disclosure.

DESCRIPTION OF THE EMBODIMENTS

Figure 1:
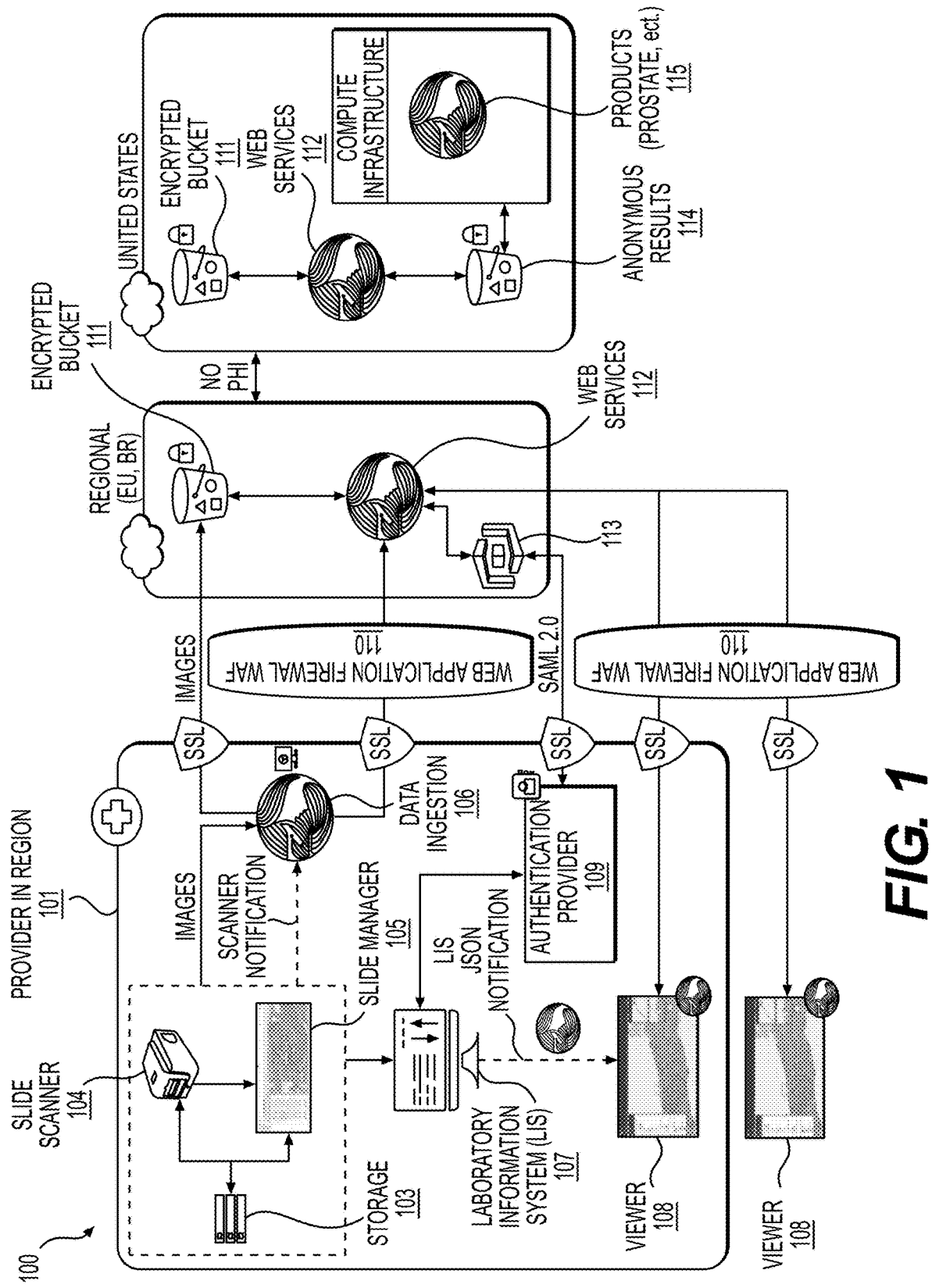
FIG. 1 is an exemplary global architecture of a platform for processing digital slides, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be places onto slides to be viewed under a microscope by a pathologist (e.g., a physician that is an expert at analyzing tissue samples to determine whether any abnormalities exist). That is, pathology specimens may be cut into multiple sections, prepared as slides, and stained for a pathologist to examine and render a diagnosis. When uncertain of a diagnostic finding on a slide, a pathologist may order additional cut levels, stains, or other tests to gather more information from the tissue. Technician(s) may then create new slide(s) which may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The present disclosure presents a platform for improving diagnosis of cancer and other diseases. The platform may integrate, for example, slide evaluation, tasks, image analysis and cancer detection artificial intelligence (AI), annotations, consultations, and recommendations in one workstation. In particular, the present disclosure describes various exemplary user interfaces available in the platform, as well as AI tools that may be integrated into the platform to expedite and improve a pathologist's work.

For example, computers may be used to analyze an image of a tissue sample to quickly identify whether additional information may be needed about a particular tissue sample, and/or to highlight to a pathologist an area in which he or she should look more closely. Thus, the process of obtaining additional stained slides and tests may be done automatically before being reviewed by a pathologist. When paired with automatic slide segmenting and staining machines, this may provide a fully automated slide preparation pipeline. This automation has, at least, the benefits of (1) minimizing an amount of time wasted by a pathologist determining a slide to be insufficient to make a diagnosis, (2) minimizing the (average total) time from specimen acquisition to diagnosis by avoiding the additional time between when additional tests are ordered and when they are produced, (3) reducing the amount of time per recut and the amount of material wasted by allowing recuts to be done while tissue blocks (e.g., pathology specimens) are in a cutting desk, (4) reducing the amount of tissue material wasted/discarded during slide preparation, (5) reducing the cost of slide preparation by partially or fully automating the procedure, (6) allowing automatic customized cutting and staining of slides that would result in more representative/informative slides from samples, (7) allowing higher volumes of slides to be generated per tissue block, contributing to more informed/precise diagnoses by reducing the overhead of requesting additional testing for a pathologist, and/or (8) identifying or verifying correct properties (e.g., pertaining to a specimen type) of a digital pathology image, etc.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (i.e., benign) or abnormal (i.e., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Hematoxylin and Eosin (H&E). For medical diagnosis, H&E is a widely used dye based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which can reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes and devices may be used to assist pathologists in detecting abnormalities that may otherwise be difficult to detect. For example, AI may be used to predict biomarkers (such as the overexpression of a protein and/or gene product, amplification, or mutations of specific genes) from salient regions within digital images of tissues stained using H&E and other dye-based methods. The images of the tissues could be whole slide images (WSI), images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues has the potential to improve patient care, while also being faster and less expensive. Computational pathology processes and devices may be used to assist pathologists in detecting abnormalities, such as floaters, that may otherwise be difficult to detect. For example, AI may be used to predict the presence of floaters from individual regions within digital images of prepared tissue samples. The images of the tissues could be whole slide images (WSI), images of tissue cores within microarrays or selected areas of interest within a tissue section. Using staining methods like H&E, these biomarkers may be difficult for humans to visually detect or quantify without the use of additional testing. Using AI to infer these biomarkers from digital images of tissues has the potential to improve patient care, while also being faster and less expensive.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Techniques discussed herein may be performed end-to-end using AI techniques, with no or minimal user intervention.

Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

The digital pathology images described above may be stored with tags and/or labels pertaining to the properties of the specimen or image of the digital pathology image, and such tags/labels may be incorrect or incomplete. Accordingly, the present disclosure is directed to systems and methods for identifying or verifying correct properties (e.g., pertaining to a specimen type) of a digital pathology image. In particular, the disclosed systems and methods may automatically predict the specimen or image properties of a digital pathology image, without relying on the stored tags/labels. Further, the present disclosure is directed to systems and methods for quickly and correctly identifying and/or verifying a specimen type of a digital pathology image, or any information related to a digital pathology image, without necessarily accessing an LIS or analogous information database. One embodiment of the present disclosure may include a system trained to identify various properties of a digital pathology image, based on datasets of prior digital pathology images. The trained system may provide a classification for a specimen shown in a digital pathology image. The classification may help to provide treatment or diagnosis prediction(s) for a patient associated with the specimen.

This disclosure includes one or more embodiments of a specimen classification tool. The input to the tool may include a digital pathology image and any relevant additional inputs. Outputs of the tool may include global and/or local information about the specimen. A specimen may include a biopsy or surgical resection specimen.

Exemplary global outputs of the disclosed tool(s) may contain information about an entire image, e.g., the specimen type, the overall quality of the cut of the specimen, the overall quality of the glass pathology slide itself, and/or tissue morphology characteristics. Exemplary local outputs may indicate information in specific regions of an image, e.g., a particular image region may be classified as having blur or a crack in the slide. The present disclosure includes embodiments for both developing and using the disclosed specimen classification tool(s), as described in further detail below.

In the field of computational pathology, information security and data privacy should be considered a priority when examining tissue specimen. Personal data and health-related information should be protected. The below description outlines an approach to protecting sensitive and legally protected information in the development and delivery of computational pathology services and products. Further, the present description outlines a security and privacy by design approach as well as production system protections for all data, including the data belonging to a medical practice, patients, and/or customers.

One embodiment of a computational pathology process or device may be an integrated computing platform offering any or all of the following:

An AI-native digital pathology slides viewer. The viewer may comprise an interactive user interface or notification dashboard. The viewer may further support the collaboration and sharing of slide images.

A suite of AI products, including products designed for different parts of the body (e.g., prostate), which may plug into different workflow steps.

A data ingestion appliance to facilitate the transfer of digital pathology slides.

FIG. 1 depicts an exemplary global architecture of a platform for processing digital slides consistent with the present disclosure. One or more embodiments may use a cloud provider such as an Infrastructure-as-a-Service (IaaS) and Platform-as-a-Service (PaaS) provider to provide a scalable, reliable, secure, available service to customers on a global scale. The exemplary global architecture 100 may include use by a provider in a region 101, and may send digital slides and images to other regions, such as the European Union or the United States. The global architecture is developed to account for compliance, reliability, security and privacy across any region.

One or more embodiments may provide any or all of the following features:
a. Automatically and securely ingest scanned images deposited by WSI scanners 104 into storage 103 and copy these images into secure cloud storage (e.g., a fully automated process).
b. Leverage the latest advances in cloud computing to automatically perform AI computations at scale once the images are received.
c. Provide a state-of-the-art experience to view the uploaded images and predictions generated by AI products.
d. Maintain strict enforcement of regulatory requirements for Protected Health Information (PHI), including the prevention of patient information from leaving its originating geography.

The product architecture is developed to account for compliance, reliability, security and privacy, in accordance with the following:

Protected Health Information (PHI) may be held in the originating region: As illustrated in FIG. 1, identifiable patient information may be kept in the region where the practice is located. To achieve this, all scanned images may be kept in an encrypted bucket 111, which may be a simple storage service (S3) encrypted bucket, physically located in any of the regions. According to one or more embodiments, a region may refer to locations having different sizes and characteristics. For example, a region may correspond to a country, a city, and/or a hospital, etc. Any metadata related to patients may also be encrypted and stored in that region.

Well-defined API endpoints for data ingestion: in order to minimize the exposure of sensitive data, a specific endpoint and a unique bucket 111 may be provided to limit the number of firewall rules to be created. This endpoint may be stable to reduce the risk of service disruption.

Leveraging authentication provider(s): one or more embodiments may integrate with an authentication provider using a protocol (e.g., Security Assertion Markup Language (SAML) 2.0 protocol) allowing an IT department to manage credentials and access for authorized accounts.

Customer segregation: uploaded images may be stored in cloud storage dedicated to an institution to prevent data leakages between customers. Other data may be multi-tenant and not necessarily segmented from other customer's data.

Within the provider in region 101 location, the global architecture 100 may include a Whole Slide Image (WSI) system 102, where WHIs are digitized and may be stored locally in a storage 103. WSIs may be scanned by slide scanner 104, and sent from the slide scanner 104 to the slide manager 105. From the WSI system 102, digitized images may be sent to either a data ingestion appliance 106 or a Laboratory Information System (LIS) 107. If the images are sent to LIS 107, a user may be notified by a JSON notification that images are available to be viewed on viewer 108.

If the images are instead sent to data ingestion appliance 106, images may be further sent through Web Application Firewall (WAF) 110 to web services 112, located outside of the originating region 101 of the slides. From web services 112, images may be sent to a web service console 113 and then back to the original region 101 for additional processing, review, or authentication by authentication provider 109. Images may also be sent through WAF 110 to a viewer 108 outside of the provider in region 101.

Alternatively, images may be sent from the data ingestion appliance 106 to a unique encrypted bucket 111. The encrypted bucket 111 may be physically located in a number of different regions, for example in the EU, Brazil or in the US. A region may be refer to geographic, institutional, or geopolitical locations, such as countries, collection of countries, states, provinces, counties, cities, municipalities, hospitals, offices, etc., having different sizes, characteristics, and/or legal or procedural practices, rules, and/or laws. Protected Health Information (PHI) associated with any of the images or slides might be prohibited from traveling between encrypted buckets 111 that are located in different regions. It may be determined, on a case-by-case basis, if PHI may travel between encrypted buckets 111 that are located in different regions based on one or more rules, practices, laws, etc., associated with the source region, the destination region, and/or any intermediate transit regions through which the data will pass during transfer. Based on the determination as to whether and which PHI and/or other data must be removed, PHI and/or other data may be partially or entirely removed at the source region before being transferred. If the encrypted bucket 111 is located within the US, images may be sent to and from web services 112, which may further send images to another encrypted bucket 114 for holding anonymous results. These anonymized results may be used in other products 115, including diagnostic tools aimed at a specific area of the body such as the prostate, etc.

One or more embodiments of the global architecture 100 relate to performing a backup of customer data on a periodic basis and keeping the records for a predetermined time period (e.g., six years) in order to provide disaster recovery capabilities.

According to one or more embodiments, customers may remain the owners of their data. Customers' data may be used to improve products and to further develop the platform and related products and services.

A cohesive Data Loss Prevention (DLP) solution may be deployed to detect any potential data breaches or leakages, monitor data flows and protect sensitive information (e.g., customer data and intellectual property).

The security standards may align with selected standards (e.g., HIPAA<ISO 27001, GDPR and HITRUST).

Access to physical offices may be controlled by a key card management system. Key card access may also control entry to restricted office areas. The logs of the key card system may be maintained in a secure log management tool that is used for monitoring, alerting, and event correlation. Physical offices also have video monitoring at all physical entry ways.

According to one or more embodiments, source code may be stored securely in a Version Control System requiring employee authentication and enabling auditability. Code changes may be peer-reviewed for quality and potential security issues. Further, component and product versioning may enable full traceability.

In addition to traditional testing, Static Application Security Testing (SAST) and Dynamic Application Security Testing (DAST) may be performed for all the components forming the final products. For maximum efficiency, these tools may be integrated within the SDLC and within a continuous integration platform.

Patch Management: A regular patching procedure and schedule may be maintained. Operating system patching may be conducted monthly for all management systems. Product and third-party software patching may be managed throughout the development of the product and deployed with each release. The process may comprise a Quality Management System.

Vulnerability management: Security tools may be utilized for conducting active security and vulnerability scans of the product and production environment. Identified issues are logged and a risk assessment is performed. A security team may conduct regular assessments, reviews, and audits of the environment. Further, the team may track and remediate vulnerability issues.

Malware prevention: Malware prevention may include the use of antivirus and malware detection tools. Network traffic may be controlled and monitored by a firewall.

Figure 2:
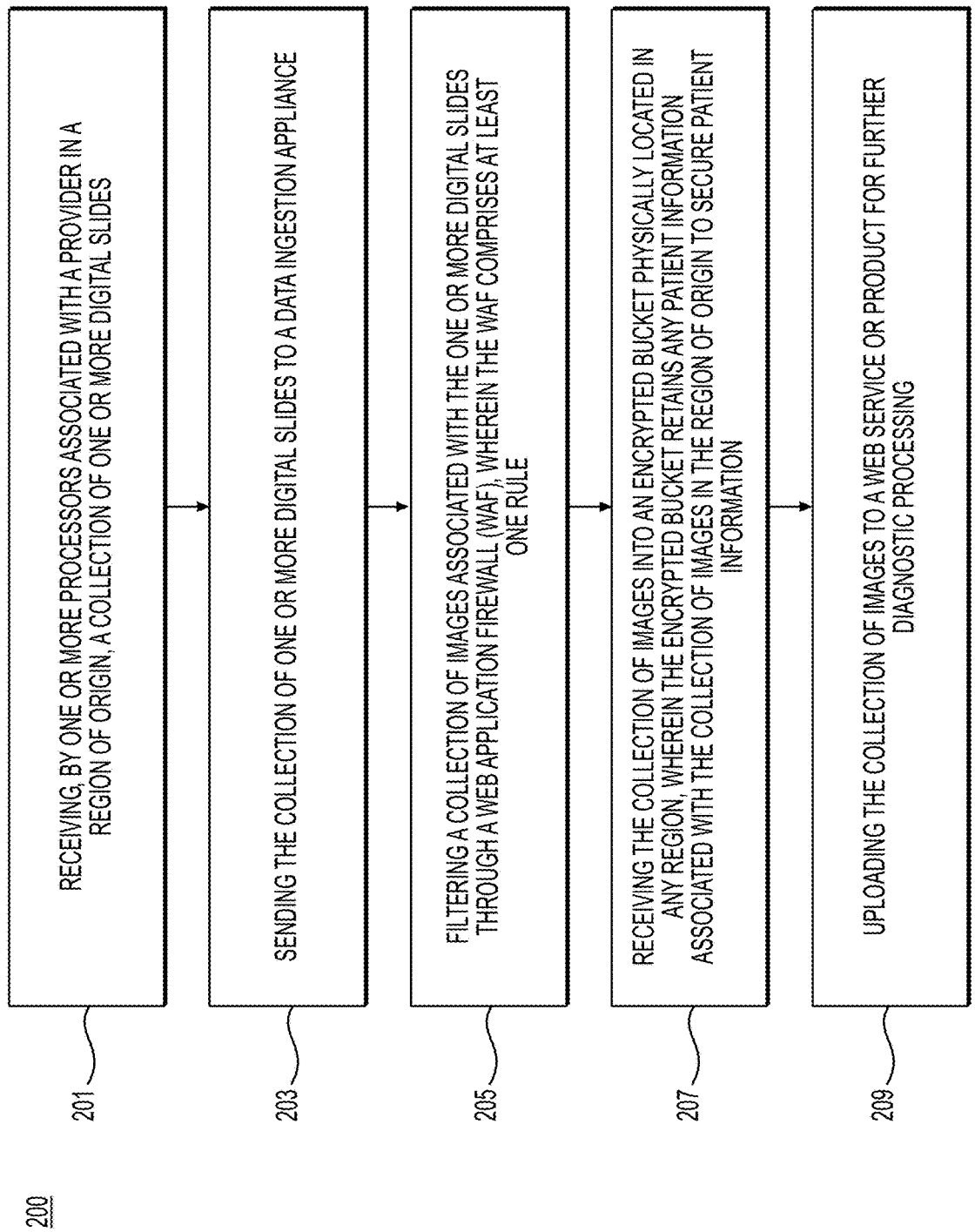
FIG. 2 is a flowchart illustrating an exemplary method for use of the platform, according to an exemplary embodiment of the present disclosure.

FIG. 2 is a flowchart illustrating an exemplary method for use of the global platform, according to an exemplary embodiment of the present disclosure. For example, an exemplary method 200 (e.g., steps 201-209) may be performed by the global architecture 100 automatically or in response to a request from a user.

According to one embodiment, the exemplary method 200 for using an integrated computing platform to view and transfer digital pathology slides using AI may include one or more of the following steps. In step 201, the method may include receiving, by one or more processors associated with a provider in a region of origin, a collection of one or more digital slides. The collection of slides may be provided by WSI system 102, as illustrated in FIG. 1 and described above.

In step 203, the method may include sending the collection of one or more digital slides to a data ingestion appliance. The data ingestion appliance, such as data ingestion appliance 106, may be local to the WSI system 102, as described below, or a standalone product. The data ingestion appliance 106 may output the collection of one or more digital slides as a collection of images.

In step 205, the method may include filtering the collection of images associated with the one or more digital slides through a WAF, such as WAF 110, wherein the WAF comprises at least one rule.

In step 207, the method may include receiving the collection of images into an encrypted bucket physically located in any region, wherein the encrypted bucket retains any patient information associated with the collection of images in the region of origin to secure patient information.

In step 209, the method may include uploading the collection of images to a web service or product for further diagnostic processing.

FIG. 3 is a workflow illustrating an exemplary method for use of the platform with an AI output, according to an exemplary embodiment of the present disclosure. For example, AI may be applied in many aspects of a complete workflow used by the platform, either automatically or in response to a request by a user.

According to one embodiment, the exemplary method 300 for using the platform with an AI output may include one or more of the following steps. In step 301, slides are scanned into the workflow. The slides may be scanned in by slide scanner 104 and stored in WSI system 102.

In step 303, an AI may be run on the input slides. The AI may incorporate not only the slide itself, but also associated patient data, such as a genetic profile, patient history, other related slides, radiology data, molecular data, clinical data, etc.

In step 305, an AI output is generated from the slide. The output may be customizable according to user wishes, and may include but is not limited to the following examples:

Case assignment: cases may be assigned to an expert pathologist based on the AI output, to inform pathologists automatically about the case, and/or to assign cases to multiple pathologists.

Case worklist: cases may be sent to a worklist to organize or prioritize cases according to urgency, to visualize cases according to importance, and/or to search cases by a desired outcome.

Case preparation: cases may be prepared to order special stains needed for a patient, to suggest clinical trials for the patient, and/or to trigger a rescan of a slide, e.g., based on poor slide quality.

Slide tray: slides may be organized within a case according to urgency or severity, to visualize slides according to importance, and/or to search cases by detected outcome.

Slide viewer: a slide may be viewed with an overlay of a graphical AI result (a conventional incorporation of AI), to summarize an AI result textually, and/or to suggest or to trigger follow-up studies.

Pathology report: a pathology report may be pre-filled with the AI results of the workflow.

FIGS. 4A-C are exemplary architectures of a data ingestion appliance and the integration of the data ingestion appliance to the platform architecture, according to exemplary embodiments of the present disclosure. An exemplary architecture of a data ingestion appliance consistent with the present disclosure may provide a Data Ingestion Appliance able to receive notifications when slides are digitized as images, then queue and upload the new images. Once ready, the acquired images may be encrypted (e.g., using TLS 1.2+) and sent to secure cloud storage where they will be processed.

The Data Ingestion Appliance may seamlessly integrate with one or more scanners, such as slide scanner 104. Data in transit may be encrypted (e.g., using TLS 1.2+ with AES-256 encryption, via industry standard HTTPS).

The Data Ingestion Appliance may be distributed as an Open Virtual Appliance (OVA) file.

In one exemplary embodiment shown in FIG. 4A, data ingestion may comprise a WSI system 102, an LIS 107, and a bridge 120. The WSI system 102 may further comprise an image management system (IMS) or slide manager 105, a storage 103, and a slide scanner 104, where all components are able to communicate and send slide images between one another.

In FIG. 4A, an integration between the LIS 107 and the slide manager 105 has been established. This interface allows for digitized slides to be accessible from the LIS 107. A bridge 120 may be deployed and configured to consume all information from the interface built from the slide scanner 104, such as the WSI system 102. The interface may be built in Health Level 7 (HL7), Fast Healthcare Interoperability Resources (FHIR), databases, Representational state transfer (REST) application programming interfaces (API), etc. Any supplemental information may be obtained from the LIS 107. From the bridge 120, images and associated information may be sent to a cloud 121.

In FIG. 4B, there is no integration between any part of the WSI system 102 and the LIS 107. In this option, the WSI system does not contain a slide manager 105. Here, the bridge 120 is deployed and configured as the main system to consume digitized images from the slide scanner 104 and the storage 103. The bridge 120 may also be used to retrieve patient and case initial metadata from the LIS 107. Bridge 120 may then send any of this information about the digitized images to the LIS 107, or may send images and associated information to the cloud 121.

In FIG. 4C, an integration exists between LIS 107 and WSI system 102. Specifically, the integration exists between the LIS 107 and the slide manager 105, which allows for digitized slides to be accessible from the LIS 107. Through this interface, patient, case and slide information may be available. The bridge 120 may be deployed and configured to consume all information from the interface built against the slide scanner 104 system. From the bridge 120, images and associated information may be sent to cloud 121.

Figure 5C:
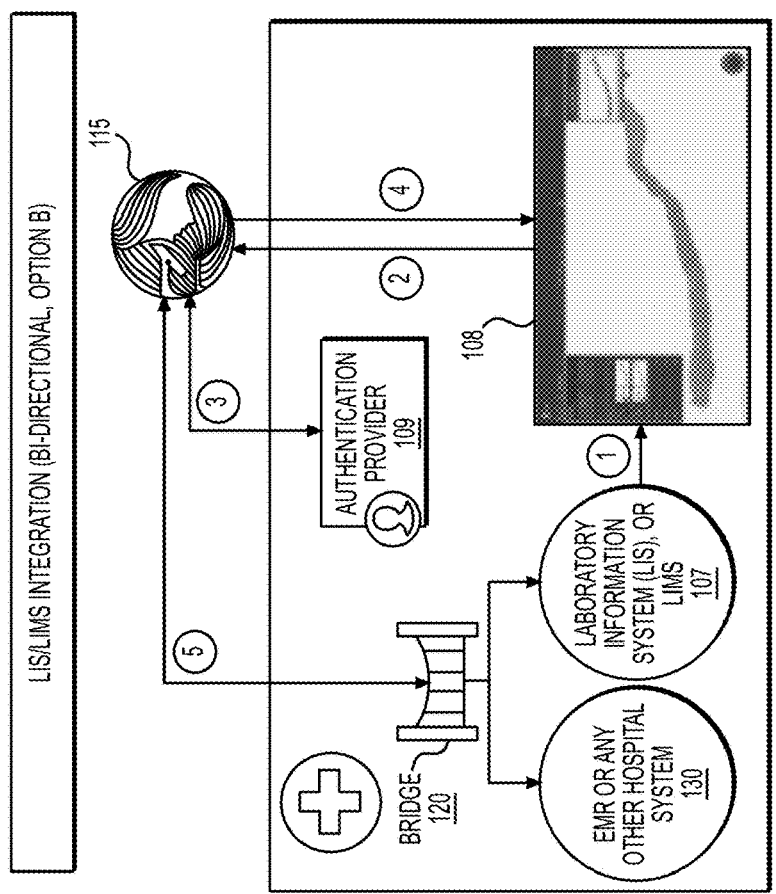
Figure 5B:
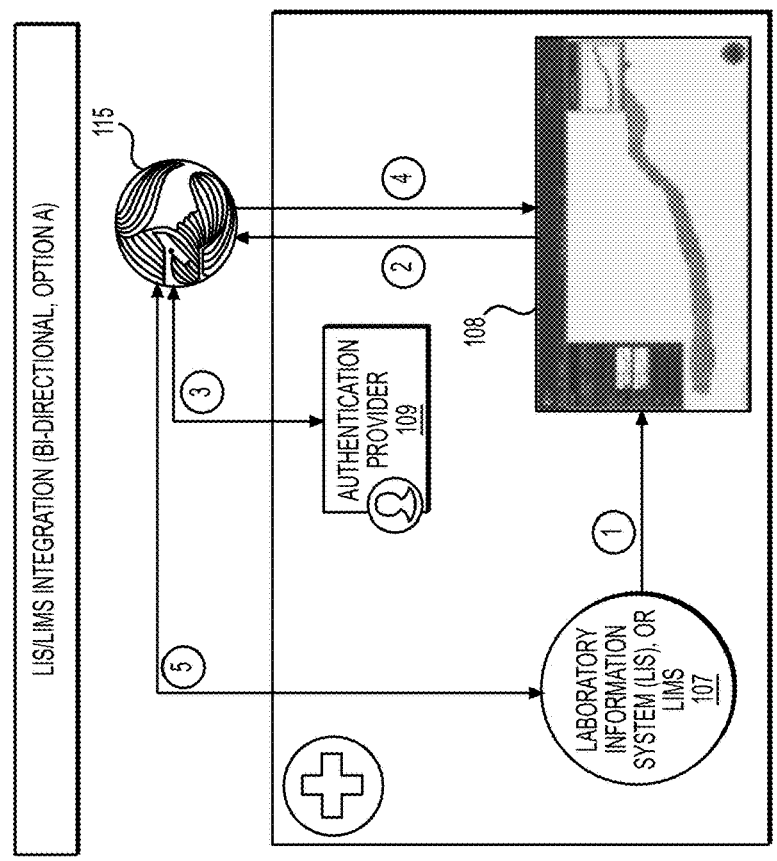

FIGS. 5A-C are exemplary architectures of a LIS and the integration of the LIS to the platform architecture or other hospital systems, according to exemplary embodiments of the present disclosure.

As shown in FIG. 5A, the LIS 107 may communicate one-way with a viewer 108. Once the viewer 108 is opened, either automatically or in response to a request from a user, a protocol such as HTTPs may request passing all information to identify a case and a patient. This information may be sent for verification by the LIS 107 to web product 115. The information may be authenticated to a hospital's authentication provider 109 using SAML or another standard for exchanging authentication. Once authenticated, the images and any associated AI results may be streamed or displayed on the viewer 108.

As shown in FIG. 5B, the LIS 107 may communicate directly with viewer 108. The web product 115 may also communicate directly with LIS 107, establishing bi-directional integration of the LIS 107. Once the viewer 108 is opened, either automatically or in response to a request from a user, a protocol such as HTTPs may request passing all information to identify a case and a patient. This information may be sent for verification by the LIS 107 to web product 115. The information may be authenticated to a hospital's authentication provider 109 using SAML or another standard for exchanging authentication. Once authenticated, the images and any associated AI results may be streamed or displayed on the viewer 108. Additionally, the LIS 107 may pull information from the web product 115—provided REST APIs.

As shown in FIG. 5C, the LIS 107 may communicate directly with viewer 108. The web product 115 may also communicate with LIS 107 via the bridge 120, establishing bi-directional integration of the LIS 107. Once the viewer 108 is opened, either automatically or in response to a request from a user, a protocol such as HTTPs may request passing all information to identify a case and a patient. This information may be sent for verification by the LIS 107 to web product 115. The information may be authenticated to a hospital's authentication provider 109 using SAML or another standard for exchanging authentication. Once authenticated, the images and any associated AI results may be streamed or displayed on the viewer 108. Additionally, the bridge 120 may be used for more sophisticated writing operations to the LI 108 or other systems, such as electronic medical records (EMR) or hospital system 130, over any protocol.

Figure 6:
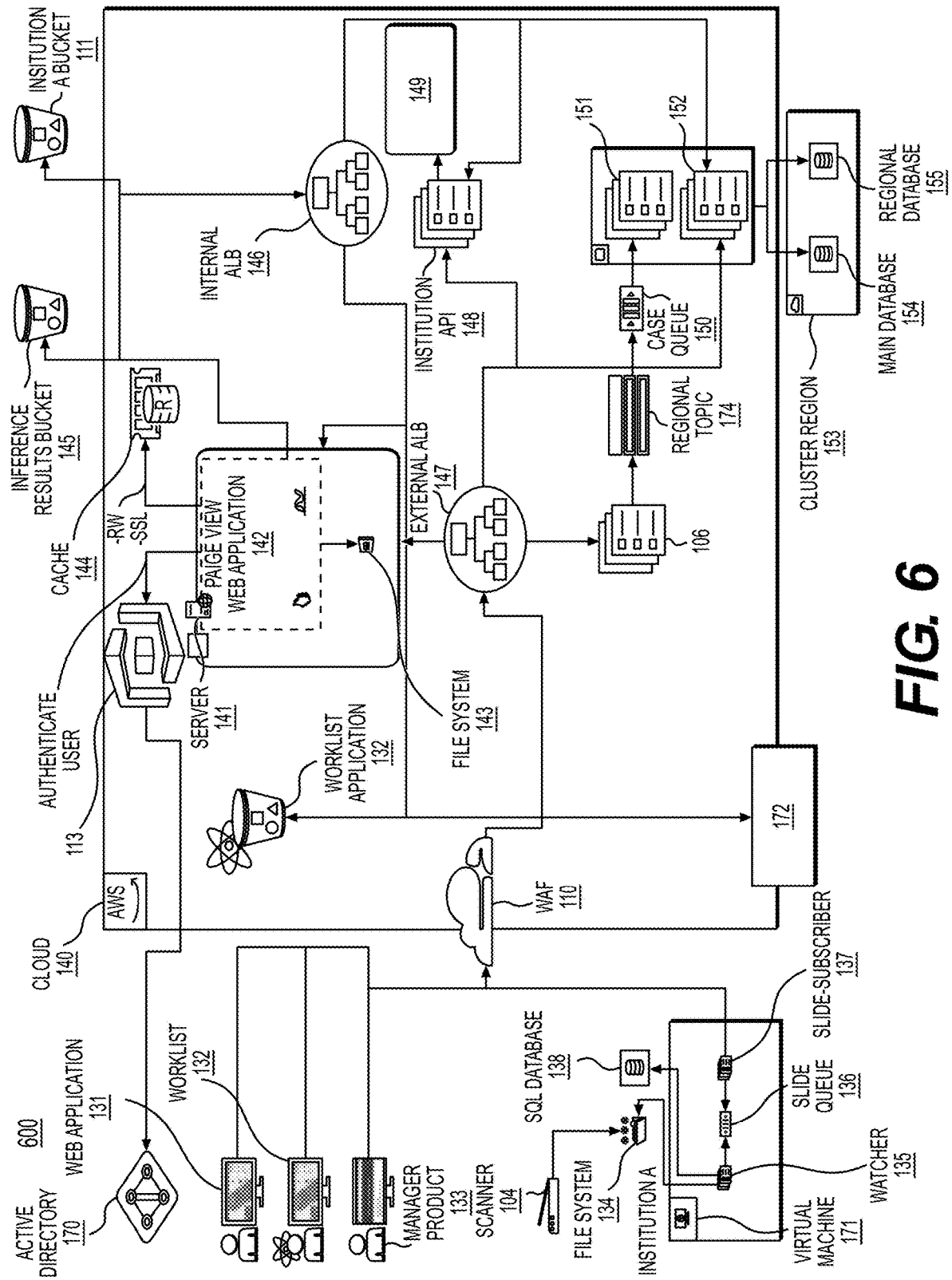
FIG. 6 is an exemplary architecture of a slide viewer, according to an exemplary embodiment of the present disclosure.

FIG. 6 is an exemplary architecture of a slide viewer, according to an exemplary embodiment of the present disclosure. The viewer may be used for in vitro diagnostic use as an aid to the pathologist to review and interpret digitized images of a pathology specimen or case, which may include protected health information (PHI) about an associated patient. For example, an embodiment of a viewer may comprise an AI-native web-based software product that facilitates improved viewing and navigating of digitized pathology images of slides. The exemplary architecture may allow a user (e.g., pathologist) to view digitized slide images or diagnostic cases.

The exemplary architecture 600 may include a number of components in a local setting as well as a number of components based in a cloud computing service, such as cloud 140. Within the local setting, there may be products such as a web application 131, a worklist 132, and a manager product 133 with a corresponding user, e.g., a pathologist, administrator, etc. Any one of web application 131, worklist 132, and/or manager product 133 may send slides or other information through slide subscriber 137 to slide queue 136. Additionally, there may be a slide scanner 104, a file system 134 and a database 138 at an institution A with virtual machine 171. The virtual machine may include a watcher 135 which may retrieve slides from file system 134 or database 138 before sending slides to a slide queue 136.

In the cloud 140, all images may need to be screened through a WAF 110. Then, slides may be sent to a cloud-based worklist 132, an internal application load balancer (ALB) 146 or external ALB 147, or to a web framework 172.

If the images are sent to internal ALB 146, the internal ALB 146 will then sent images to an institution API 148. In turn, the institution API 148 may send images to a SQL instance 149, where they may be stored. The institution API 148 may also send the images to a case API 152. If requested, either automatically or in response to a request from a user, the case API 152 will send images to a cluster region 153, which comprises a main database 154 and a regional database 155.

If the images are sent to external ALB 147, they may then be sent on to a data ingestion appliance 106, to a regional topic 174. From the regional topic 174, images may be sent to a case queue 150 and then a case subscriber 151, or to case API 152. As described above, case API 152 may send images to a cluster region 153, which comprises a main database 154 and a regional database 155. Alternatively, images may be sent from the external ALB 147 directly to the case API 152, or to instance 149. Further, the external ALB 147 may send images directly to case queue 150.

External ALB may also send images to worklist 132 or to server 141. Server 141 may comprise web application viewer 142 and file system 143. File system 143 may store slide images on the server 141. The server 141 may send images on to web service console 113 after a user is authenticated, which in turn may send images from the cloud 140 to the active directory 170.

From the web application viewer 142, images may also be sent to cache 144, which stores project and user information along with application logs, or to one or more buckets. For example, one bucket may be the inference result bucket 145, and another may be a bucket 111 associated with institution A in region 101. Alternatively, the web application viewer may send images back to an internal ALB 146.

Figure 7:
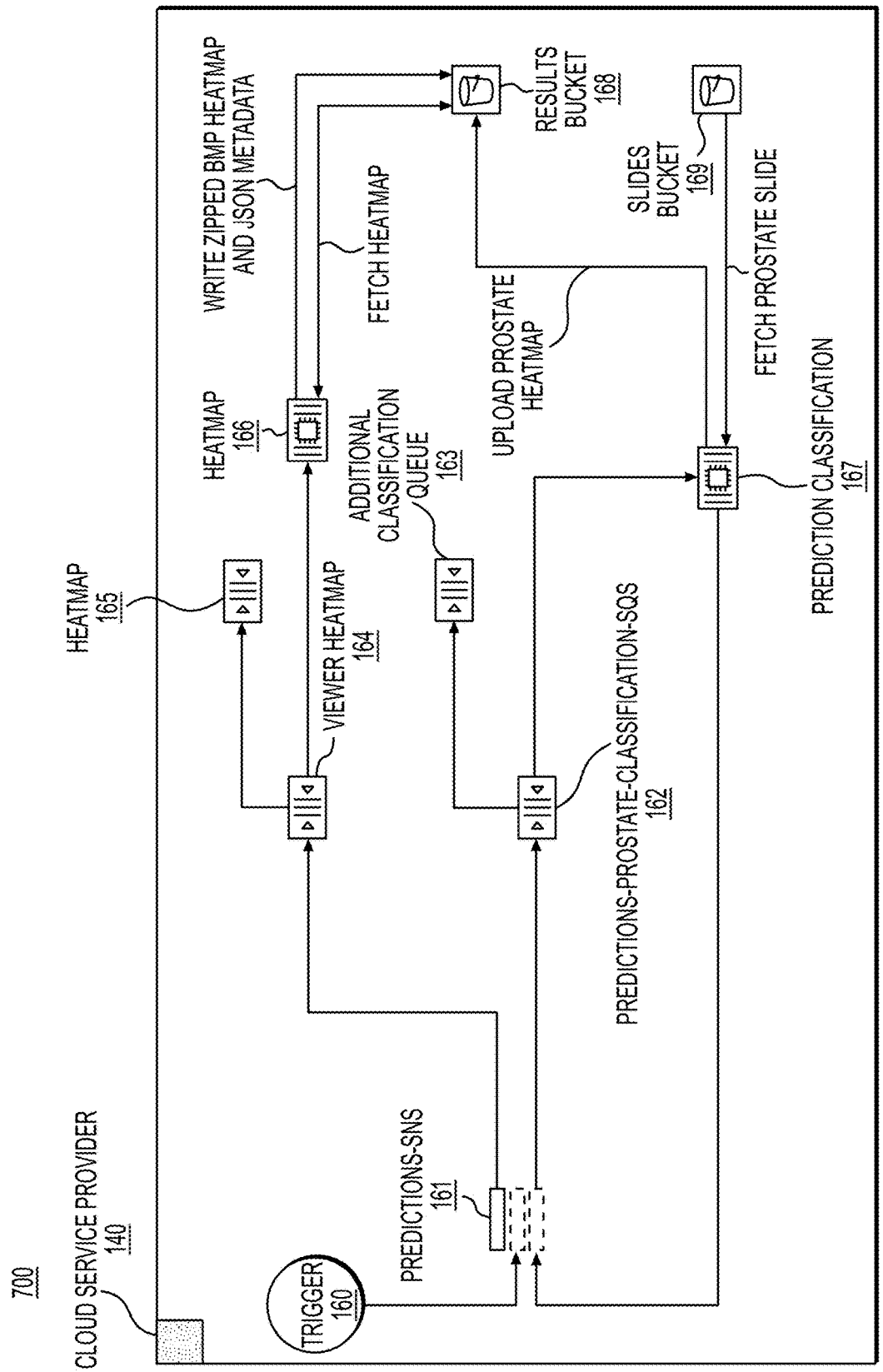
FIG. 7 is an exemplary architecture of an AI computer, according to an exemplary embodiment of the present disclosure.

As illustrated in FIG. 7, one or more embodiments may provide an architecture for computational pathology processes and devices (e.g., prostate cancer detection). The architecture may be used to apply AI and machine learning models to images from slides which include specimens taken from part(s) of the body, which may use initial metadata associated with the patient, and may generate additional metadata (e.g., heatmap, points of interest, virtual staining, confidence metrics, disease type data, progression estimates) related to the AI and machine learning models. A heatmap is only one possible return value of the computational pathology processes and devices. While a heatmap is described in detail below, other return values may include an overlay image, text, or other information.

A heatmap may be a two-dimensional (2D) image that identifies a probability of cancer for each area of the image from the slide. For example, each pixel of the image may be assigned a value between 0 and 1, with a higher number corresponding to a higher probability of cancer in that particular area of the image.

In response to a trigger (e.g., files being uploaded or scanned, a user input, etc.), one or more messages may be enqueued into a notification service. The messages may be processed and sent to a classification queue and forwarded to a classification worker service. If an error occurs and a message is unable to be processed, the message may be sent to a dead letter queue to be later analyzed.

For every message received at the classification worker service, the slide (e.g., prostate slides) may be retrieved and a computation may be performed. The computation may be performed using a machine learning model that is trained to identify the biomarker(s) of interest from relevant tissue (e.g., cancer tissue), with irrelevant tissue excluded from analysis. After the computation is performed, a heatmap that shows a likelihood of cancer in any part of the image may be created and uploaded (e.g., prostate heatmap). Further, after the computation, the classification worker service may push a notification back to the notification service indicating whether the heatmap was prepared or whether the process failed.

Further, the notification service may, based on the notification received from the classification worker service, send a message to a viewer heatmap queue. The messages may then be processed sequentially or in parallel by the heatmap queue and forwarded to a heatmap worker service. If an error occurs and a message is unable to processed, the message may be sent to a dead letter queue to be later analyzed.

For every message received at the heatmap worker service, a heatmap may be retrieved from a results bucket and a computation may be performed. According to an embodiment, after retrieving the heatmap from the results bucket, the heatmap worker service may create a zipped bmp heatmap and json metadata and pushing it to the results encrypted bucket. According to another embodiment, the heatmap worker service may send the heatmap to the results bucket along with a zipped bmp heatmap and json metadata.

One or more embodiment may provide any or all of the following features:

Encrypt data in-transit (e.g., using TLS 1.2+). This may include any one or any combination of data being transmitted to its services, data transmitted within the ecosystem, and data being transmitted back to customers.

Store data at-rest, including PHI (e.g., AES-256 encryption).

Encryption keys are stored in a Key Management System (KMS) (e.g., a secure and resilient service that utilizes hardware modules built to FIPS 140-2 standards).

Enforce full-disk (pre-boot) encryption of any or all devices where customers' data is treated and received.

Computational pathology detection processes and devices may be provisioned behind a Web Application Firewall (WAF), which monitors incoming HTTP traffic and filters unpermitted traffic to protect against malicious attacks (e.g., injections, DDOS, etc.).

For an increased level of security, one or more embodiments may separate production resources from administrative and development resources. For example, granular access controls may be used to prohibit customer data from leaving the production enclave.

The architecture 700 of the computational pathology processes and devices may be based in a cloud 140. As described above, the processes may begin with a response to a trigger 160, which may send a message to a prediction module 161. The prediction module 161 may send a prediction to a viewer heatmap 164, which may use the prediction to create an additional heatmap 165 or heatmap 166. Heatmap 166 may be zipped and sent to a results bucket 168, and may additionally fetch a heatmap from the results bucket 168.

Prediction module 161 may also send an uploaded slide to a prediction classification module 162. The prediction classification module 162 may either send the slide to an additional classification queue 163 or to a prediction classification 167. From the prediction classification 167, an uploaded heatmap may be sent to results bucket 168. Alternatively, the prediction classification 167 may fetch a prostate slide from slide bucket 169.

Figure 8A:
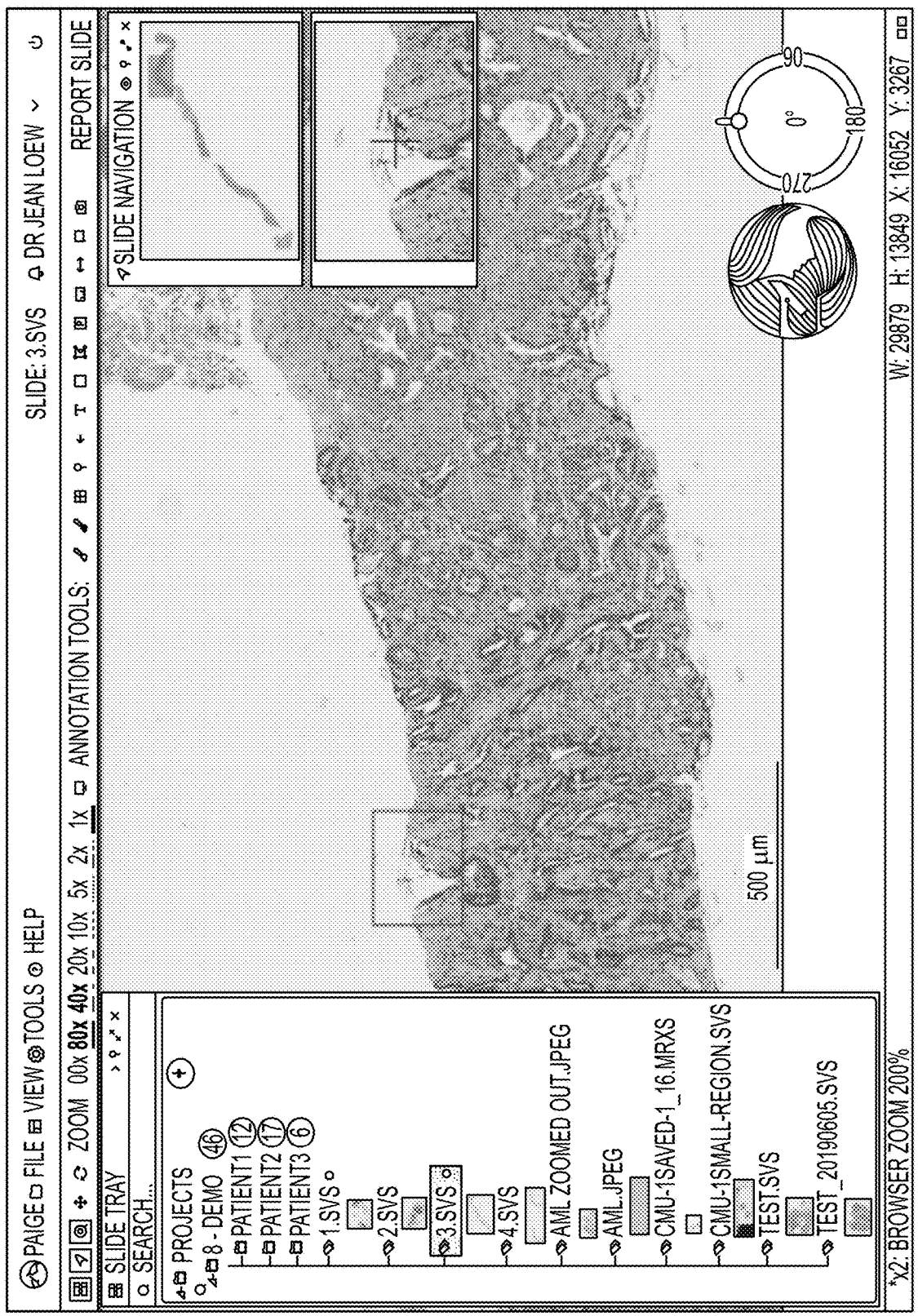
FIGS. 8A-C are exemplary displays from the slide viewer.
Figure 8B:
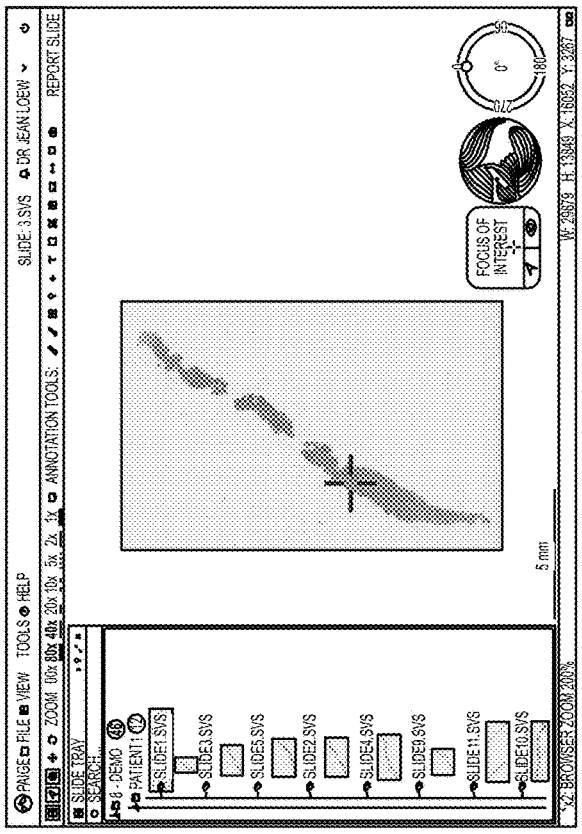
Figure 8C:
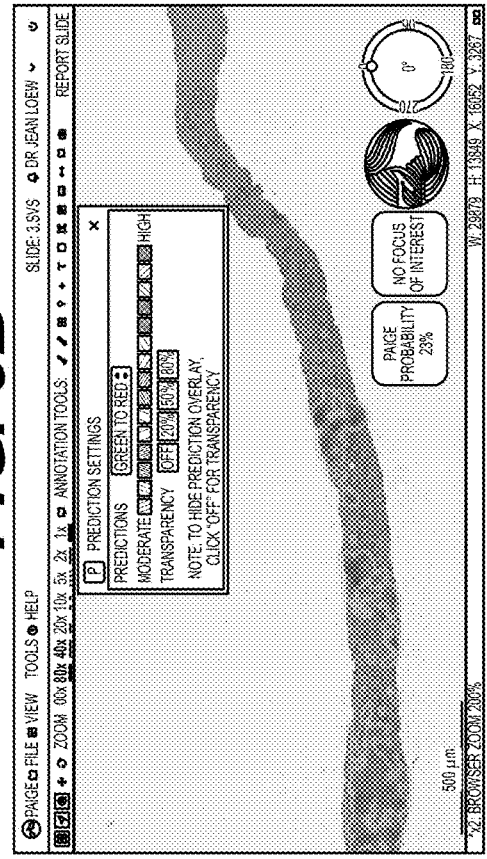

FIGS. 8A-C are exemplary displays from a slide viewer.

In FIG. 8A, an exemplary screenshot of one embodiment of the slide viewer as described above is shown. In particular, one embodiment of the viewer may comprise an AI-native web-based software product that facilitates improved viewing and navigating of digitized pathology images of slides. The viewer may display digital scans of surgical pathology glass slides prepared from tissue at resolutions up to 400× magnification. These digitized images may then be reviewed and interpreted by pathologists. FIG. 8A shows an exemplary tissue with an inset image identifying a field of view of interest for further inspection and navigation.

In FIG. 8B, a second exemplary screenshot of an embodiment of the slide viewer as described above is shown. The exemplary screenshot provides a location of one or more points of interest within a tissue, according to an exemplary embodiment of the present disclosure. An AI product of the present disclosure may comprise a diagnostic decision support tool designed to identify foci that are suspicious for cancer on digital images of histopathology slides from biopsies (e.g., prostate needle biopsies). The tool may be designed for identifying various types of cancers, or a single type of cancer (e.g., prostate cancer). The tool may detect a concerning morphology, and provide a notification to direct the pathologist's attention to foci suspicious for cancer.

According to one or more embodiments, there is provided a diagnostic decision support tool that includes in vitro diagnostic medical device software, derived from a deterministic deep learning model that has been trained with digitized biopsy slides (e.g., digitized hematoxylin & eosin (H&E) prostate needle biopsy slides) seen and diagnosed at a medical center (e.g., cancer center).

According to one or more embodiments, there is provided a diagnostic decision support tool that identifies digitized biopsy images (e.g., digitized H&E prostate needle biopsy images) that are suspicious for cancer (see disclosure below) to draw the pathologist's attention to suspicious regions of the slide for review. For each analyzed slide, the tool can (1) identify whether or not the provided image is suspicious for cancer; (2) provide the location of one or more points of interest in which nearby tissue has a relatively higher suspicion for cancer than other locations; and (3) generate an additional image containing the devices predicted likelihood of cancer across the entire tissue.

FIG. 8C is an exemplary screenshot of a computational pathology device generating an additional image containing the device's predicted likelihood of cancer across an entire tissue, also known as a heatmap. The heatmap may be one of several return values of the computational pathology platform, as described in detail above.

Figure 9:
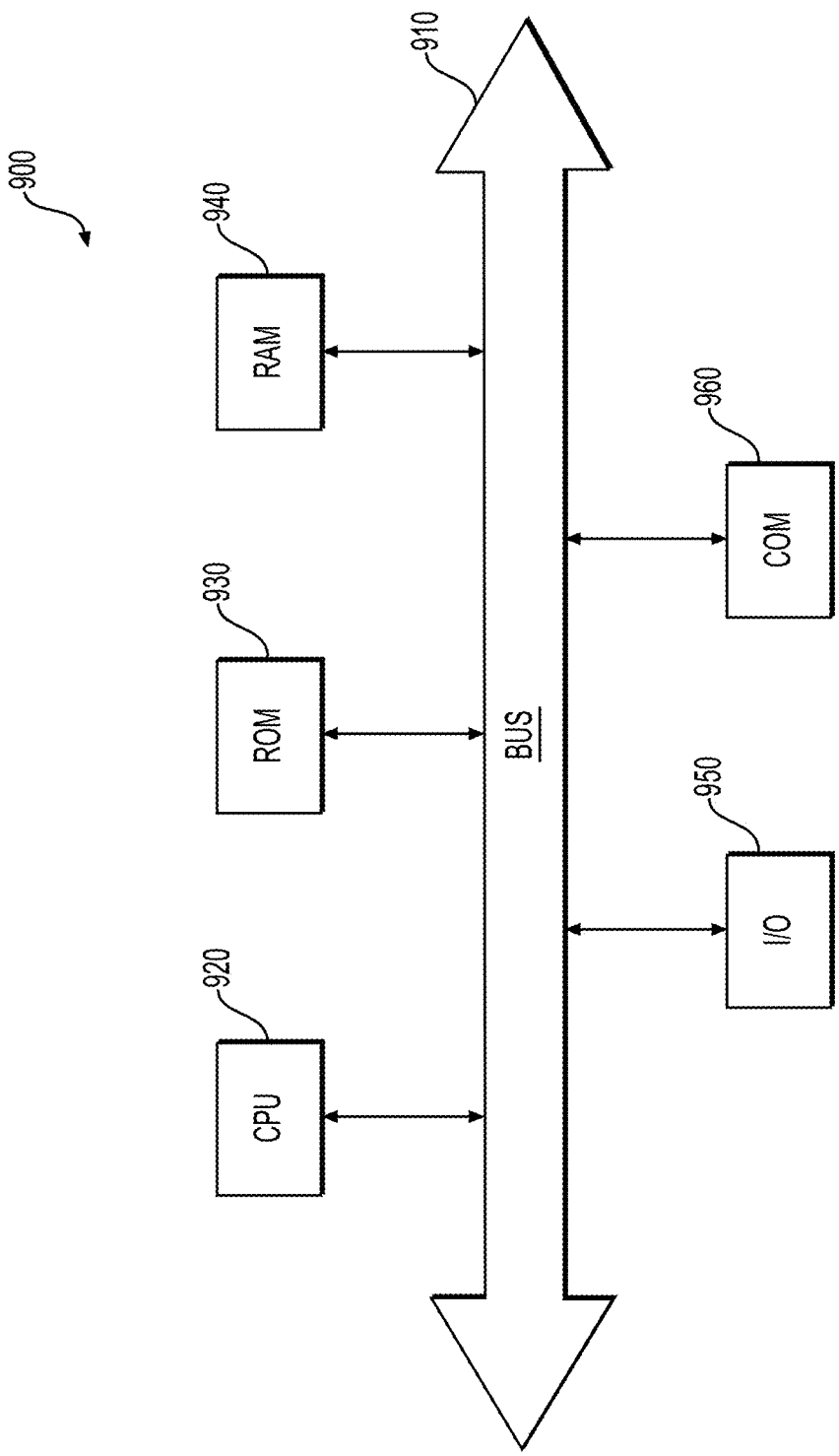
FIG. 9 depicts an example system that may execute techniques presented herein.

As shown in FIG. 9, device 900 may include a central processing unit (CPU) 920. CPU 920 may be any type of processing device including, for example, any type of special purpose or a general-purpose microprocessor device. As will be appreciated by persons skilled in the relevant art, CPU 920 also may be a single processor in a multi-core/multiprocessor system, such system operating alone, or in a cluster of computing devices operating in a cluster or server farm. CPU 920 may be connected to a data communication infrastructure 910, for example a bus, message queue, network, or multi-core message-passing scheme.

Device 900 may also include a main memory 940, for example, random access memory (RAM), and may also include a secondary memory 930. Secondary memory 930, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 930 may include similar means for allowing computer programs or other instructions to be loaded into device 900. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 900.

Device 900 also may include a communications interface ("COM") 960. Communications interface 960 allows software and data to be transferred between device 900 and external devices. Communications interface 960 may include a model, a network interface (such as an Ethernet card), a communications, a PCMCIA slot and card, or the like. Software and data transferred via communications interface 960 may in the form of signals, which may be electronic, electromagnetic, optical or other signals capable of being received by communications interface 960. These signals may be provided to communications interface 960 via a communications path of device 900, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 900 may also include input and output ports 950 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A method, the method comprising:
   storing a whole slide image in a first encrypted bucket, the whole slide image being associated with a geographic region and depicting a medical sample associated with a patient;
   determining, by artificial intelligence, whether portions of the medical sample are suspicious for disease;
   generating metadata associated with the whole slide image based on whether portions of the medical sample are suspicious for disease; and
   storing the metadata in a second encrypted bucket.

2. The method of claim 1, further comprising:
   receiving a request to transfer the whole slide image to a second geographic region; and
   removing data from the whole slide image and/or the metadata based on one or more rules associated with the second geographic region to generate a modified whole slide image and modified metadata.

3. The method of claim 1, further comprising:
   receiving a request for the whole slide image from a client device; and
   in response to determining that the client device is located in a first geographic region, providing the whole slide image and the metadata to the client device.

4. The method of claim 1, further comprising:
in response to determining that a client device is not located in the first geographic region, processing the whole slide image to determine a second whole slide image.

5. The method of claim 1, wherein storing the whole slide image further comprises performing automatic artificial-intelligence based ingestion of the whole slide image.

6. The method of claim 1, wherein determining whether portions of the medical sample are suspicious for disease comprises determining a heatmap; and storing the heatmap in the second encrypted bucket.

7. The method of claim 1, wherein generating metadata comprises determining a heatmap comprising a graphical prediction of a likelihood of disease in the medical sample.

8. The method of claim 1, wherein determining whether portions of the medical sample are suspicious for disease is performed at least in part based on patient metadata.

9. A system for processing an electronic image corresponding to a specimen, the system comprising:
at least one memory storing instructions; and
at least one processor configured to execute the instructions to perform operations comprising:
storing a whole slide image in a first encrypted bucket, the whole slide image being associated with a geographic region and depicting a medical sample associated with a patient;
determining, by artificial intelligence, whether portions of the medical sample are suspicious for disease;
generating metadata associated with the whole slide image based on whether portions of the medical sample are suspicious for disease; and
storing the metadata in a second encrypted bucket.

10. The system of claim 9, the operations further comprising:
receiving a request to transfer the whole slide image to a second geographic region; and
removing data from at least one of the whole slide image and the metadata based on rules associated with the second geographic region to generate a modified whole slide image and modified metadata.

11. The system of claim 9, the operations further comprising:
determining whether a client device is located in a first geographic region; and in response to determining that the client device is located in the first geographic region, providing the whole slide image and the metadata to the client device.

12. The system of claim 9, the operations further comprising:
determining whether a client device is located in the first geographic region; and
in response to determining that the client device is not located in the first geographic region, processing the whole slide image to determine a second whole slide image, and processing the metadata to produce modified metadata.

13. The system of claim 9, wherein storing the whole slide image comprises performing automatic artificial-intelligence based ingestion of the whole slide image.

14. The system of claim 9, further comprising: wherein determining whether portions of the medical sample are suspicious for disease comprises determining a heatmap; and storing the heatmap in the second encrypted bucket.

15. The system of claim 9, wherein determining whether portions of the medical sample are suspicious for disease is performed at least in part based on patient metadata.

16. A non-transitory computer-readable medium storing instructions that, when executed by a processor, cause the processor to perform operations comprising:
storing a whole slide image in a first encrypted bucket, the whole slide image being associated with a geographic region and depicting a medical sample associated with a patient;
determining, by artificial intelligence, whether portions of the medical sample are suspicious for disease;
generating metadata associated with the whole slide image based on whether portions of the medical sample are suspicious for disease; and
storing the metadata in a second encrypted bucket.

17. The non-transitory computer-readable medium of claim 16, the operations further comprising receiving a request to transfer the whole slide image to a second geographic region; and removing data from at least one of the whole slide image and the metadata based on one or more rules associated with the second geographic region to generate a modified whole slide image and modified metadata.

18. The non-transitory computer-readable medium of claim 17, the operations further comprising: providing the modified whole slide image and modified metadata for transfer to the second geographic region.

19. The non-transitory computer-readable medium of claim 16, the operations further comprising:
determining whether a client device is located in a first geographic region; and
in response to determining that the client device is located in the first geographic region, providing the whole slide image and the metadata to the client device.

20. The non-transitory computer-readable medium of claim 16, the operations further comprising:
determining whether a client device is located in the first geographic region; and
in response to determining that the client device is not located in the first geographic region, processing the whole slide image to determine a second whole slide image, and processing the metadata to produce modified metadata, the processing of the whole slide image and the processing of the metadata being based upon one or more rules associated with the first geographic region.

* * * * *